United States Patent [19]

Ramachandran et al.

[11] Patent Number: 5,043,461
[45] Date of Patent: Aug. 27, 1991

[54] PROCESS FOR THE PRODUCTION OF OXIDES

[75] Inventors: Ramakrishnan Ramachandran, Allendale; Mark J. Andrecovich, Somerville; Donald L. MacLean, Annandale; Donald P. Satchell, Jr., Summit, all of N.J.

[73] Assignee: The BOC Group, Inc., New Providence, N.J.

[21] Appl. No.: 518,377

[22] Filed: May 3, 1990

Related U.S. Application Data

[63] Continuation-in-part of Ser. No. 304,055, Jan. 30, 1989, Pat. No. 4,943,650.

[51] Int. Cl.$^5$ .................. C07D 301/08; C07D 301/10
[52] U.S. Cl. ............................ 549/523; 549/534; 549/535; 549/536; 549/538
[58] Field of Search ............... 549/534, 535, 536, 538, 549/523

[56] References Cited

U.S. PATENT DOCUMENTS 4,875,909  10/1989  Kakimoto et al. ............. 549/538 X Primary Examiner—Joseph Paul Brust
Attorney, Agent, or Firm—Robert I. Pearlman; Coleman R. Reap; Carol A. Nemetz

[57] ABSTRACT

An improved process for the production of oxides from hydrocarbons by reaction with oxygen, air or a gas enriched in oxygen relative to air, preferably the latter, in the presence of a suitable catalyst. An alkane, e.g. propane, is converted to an alkene in a catalytic dehydrogenator. The product stream is introduced into an oxidation reactor. Product formed therein is recovered in a conventional quench tower. The pressure of the gaseous effluent from the quench tower is raised and it is introduced into an absorber/stripper unit to form a recycle stream containing unreacted alkane and alkene as well as a minor amount of oxygen, typically 1-2 percent by volume, and a waste stream comprising the remainder of the quench tower gaseous phase. The recycle stream enters a selective oxidation unit wherein oxygen is removed, and the product recycled to the dehydrogenator. Flammability of the quench tower gaseous effluent and the waste stream from the absorber/stripper is minimized by assuring that the nonflammability index (NFI) thereof is within certain limits. Desired NFI, related to the total hydrocarbon content, may be achieved by the addition thereto of a gaseous flame suppressor. The gaseous flame suppressor, removed with the absorber/stripper unit waste stream, may advantageously be combusted to provide energy. A PSA unit may remove excess hydrogen from the dehydrogenator effluent. The dehydrogenator may be a multistage dehydrogenator.

19 Claims, 7 Drawing Sheets

FIG. I
(PRIOR ART)

PROCESS FOR THE PRODUCTION OF OXIDES

RELATED APPLICATIONS

This application is a continuation-in-part of U.S. patent application Ser. No. 07/304,055, filed Jan. 30, 1989, now U.S. Pat. No. 4,943,650, patented Jul. 24, 1990.

FIELD OF THE INVENTION

The present invention is directed to a process for producing oxides from alkanes and an oxygen-containing gas in the presence of a suitable catalyst under conditions which achieve high efficiency and selectivity toward the desired product.

BACKGROUND OF THE INVENTION

The production of oxides by oxidation of an appropriate alkane in the presence of suitable catalyst is well known.

Brian J. Ozero, *Handbook of Chemicals Production Processes*, edited by Robert Meyers, McGraw Hill Book Co. (1986) at Chapter 1.5, discusses cyclic processes using both oxygen and air as oxidant for the production of ethylene oxide (EO) from ethylene. In these processes, the alkene is oxidized in a multitubular catalytic reactor in vapor phase. The reactor off gases are cooled and scrubbed with water in an absorber to recover ethylene oxide which is sent to the recovery section for further purification.

In the oxygen-based process described by Ozero, the scrubber off gases are divided into three parts which are: i) recycled to the reactor, ii) vented and iii) sent to a separator for carbon dioxide removal and recycle of the remaining hydrocarbons. This process suffers from several disadvantages. For example, the oxygen-based ethylene oxide process requires a separate carbon dioxide removal unit and a purge to remove argon to prevent its accumulation.

In the air-based process described by Ozero, the scrubber off gases are sent to a second reactor, which is the purge reactor, where additional unreacted ethylene is reacted using a higher air to ethylene ratio, foregoing some EO selectivity. The reactor off gases are again passed through another water scrubber to recover EO produced. It is known that the volume of hydrocarbons purged, when utilizing air as a source of oxygen, requires that the purge scrubber off gases be incinerated to remove any remaining hydrocarbons in order to meet environmental regulations. In this air-based process, an additional purge oxidation reactor, a water scrubber, and an effluent incinerator are required, as well as a greater volume of catalyst. Also, both this and the oxygen-based process use the expensive ethylene as the raw material. The processes described by Ozero are limited to either pure oxygen or air.

More recently, Khoobiar et al., in U.S. Pat. No. 4,609,502 disclosed a cyclic process for producing acrylonitrile using propane as a starting material which is initially dehydrogenated catalytically in the presence of steam to form propylene. This is in contrast to most conventional dehydrogenation processes which avoid steam primarily due to the costs involved. After ammoxidation, the effluent is quenched, the desired product removed, and the off-gases, including propylene and propane, are sent to an oxidation reactor to remove oxygen by selective reaction with hydrogen to form water vapor. The gas mixture exiting the selective oxidation reactor includes substantial amounts of methane, ethane and ethylene, which are by-products of dehydrogenation, and unreacted propylene in addition to carbon oxides. As an option, this gas mixture is split and a portion is sent to a separator which removes only carbon dioxide. A portion of the effluent from the separator is purged to remove light hydrocarbons. The nonpurged stream is mixed with the remainder of the oxidator effluent, fresh propane and steam, if necessary, and sent to the dehydrogenator where the propane is converted to propylene. Another option is to cool and liquify the $C_3$ hydrocarbons therefrom and then vaporize them prior to recycle.

The aforementioned process suffers from several disadvantages. For example, there is no practical way to selectively remove by-products of propane dehydrogenation, such as methane, ethane, ethylene and the like, thereby preventing their accumulation in the system other than by removing them in the purge stream. The removal of these gases in a purge stream will result in a loss of some of the circulating propane and propylene. As the process is being carried on in a continuous manner, this loss of starting material causes a significant decrease in the yield of propylene. As mentioned above, propane and propylene can be recovered from the purge stream prior to venting. This requires additional refrigeration apparatus to cool and liquify propylene and propane. The separated $C_3$ hydrocarbons must be vaporized prior to recycle. These operations add to the capital costs and power requirements of the process.

Another disadvantage of the Khoobiar et al. process stems from the use of the selective oxidation reactor to treat the gaseous effluent from the quencher. The gases exiting the quencher are at ambient temperature and must be heated prior to introduction into the oxidation reactor in order to promote oxygen removal. Because there is a significant amount of oxygen in the quench effluent, the heat of reaction generated in the oxidation reactor can result in excessive temperatures in the system. There are three options to alleviate this problem. First, the amount of oxygen entering the oxidation reactor can be reduced by other means. Second, multiple reactors can be utilized with a cooling means between each pair of reactors. Third, a portion of the effluent from the reactor is passed through a cooling means and recycled to the feed to reduce the internal temperature of the reactor. None of these measures is attractive from the viewpoint of cost and efficiency.

The oxidation reactor in the Khoobiar et al. process is operated with oxidation catalysts such as noble metals (e.g., platinum). Olefins and carbon monoxide, which are generated in the dehydrogenation reactor, are known to deactivate these catalysts, as disclosed in *Catalytic Processes and Proven Catalysts*, Charles L. Thomas, Academic Press (1970) pp. 118-119. Accordingly, multiple oxidation reactors must be used to allow for frequent regeneration of the catalyst which represents yet another addition to production costs (U.S. Pat. No. 4,609,502, column 4, lines 51-56).

It is therefore apparent that the industry is still searching for a cost effective process of converting hydrocarbons into oxides. Applicants have discovered a process which is cost effective and in which the disadvantages of the aforementioned systems are substantially reduced or eliminated. Moreover, in comparison to conventional processes, the thermal requirements of Applicants' process are markedly reduced.

SUMMARY OF THE INVENTION

A process is disclosed for the production of oxides comprising converting a gaseous alkane to the corresponding alkene in a dehydrogenator, reacting the alkene in an oxidation reactor with an oxygen-containing gas, preferably oxygen-enriched air in the presence of a suitable catalyst to form the desired product. The product stream is quenched with a liquid to form a liquid phase containing the desired product and a gas phase which is passed under pressure into an absorber/stripper unit which removes carbon monoxide, carbon dioxide, oxygen, nitrogen, when present, and lower hydrocarbons therefrom. The product stream from the absorber unit is passed into a selective oxidation unit where the remainder of the oxygen is removed. The effluent from the selective oxidation unit is recycled to the dehydrogenator with fresh alkane feed. The use of the absorber/stripper unit and, consequently, a very economical selective oxidation unit requires processing of a potentially very flammable mixture. Flammability is kept to well within the limits of safety by maintaining the hydrocarbon content of the streams entering the compressor at a certain level by adjusting process parameters and, if necessary, the addition of a gaseous flame suppressor, selected from methane and ethane, to the quench tower gaseous effluent. When the gaseous flame suppressor is added, the effluent from the absorber unit may be incinerated to recover energy therefrom.

DESCRIPTION OF THE PREFERRED EMBODIMENTS

The process of this invention is applicable to the synthesis of oxides. In each instance, an alkene is reacted with an oxygen-containing gas comprising pure oxygen, air or a gas enriched in oxygen relative to air in the presence of a suitable catalyst. The term "suitable catalyst" indicates a catalyst that will catalyze the production of the desired product, e.g. ethylene oxide from ethylene or propylene oxide from propylene, under the conditions utilized in the reactor.

In the interest of brevity, the subject process will be described with reference to the production of propylene oxide from propane, but is in no way intended to be limited thereto.

Figure 1:
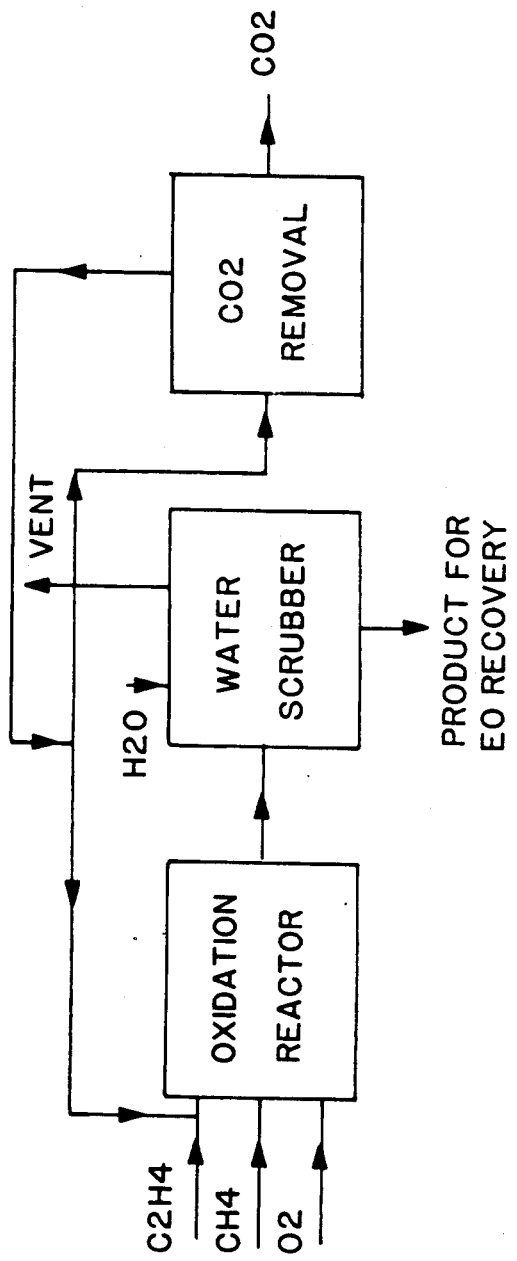
FIG. 1 illustrates in a block diagram a prior art process of producing ethylene oxide using oxygen.
Figure 2:
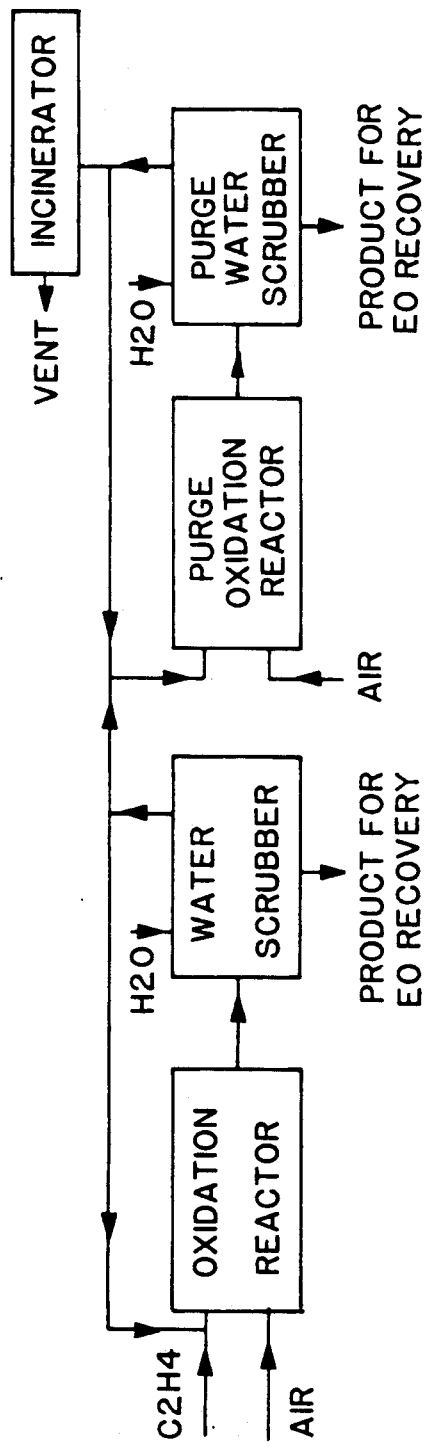
FIG. 2 illustrates in a block diagram a prior art process of producing ethylene oxide using air.

Turning to the drawings, a process currently utilized commercially to produce oxides such as ethylene oxide, is illustrated in FIGS. 1 and 2. In FIG. 1, ethylene and oxygen are fed into a conventional reactor containing a suitable oxidation catalyst; in FIG. 2, ethylene and air are similarly fed. The reactor may be of any conventional fixed or fluidized bed design, typically the former. Such processes typically employ a recycle step to increase the overall process efficiency. The oxygen concentration in the feed to the reactor is adjusted to maximize the selectivity to the desired product.

In the oxygen-based process, shown in FIG. 1, methane is added continuously to the reactor as a flame suppressor to compensate for the loss in the purge. The oxidation reactor off gases are sent to a water scrubber to remove products for ethylene oxide recovery. The scrubber off gases are divided into three parts: a first part is recycled back to the reactor, a second part is vented, and a third part is sent to a $CO_2$ removal unit. After removing $CO_2$, the off gases of the third part are sent back to the reactor. The purge is essential to prevent any argon build up in the system. Since there is no other way to remove inerts from the system, one cannot use air or oxygen-enriched air as the oxidant feed since the large volume required to purge the nitrogen would cause excessive loss of feed hydrocarbon, ethylene.

In the air-based process, shown in FIG. 2, ethylene and air are fed into the oxidation reactor. The reactor products are water scrubbed to remove the ethylene oxide produced. A part of the scrubber off gases are recycled back to the reactor while the remainder is sent to a second reactor. Additional air is added to this second reactor to achieve an air-to-ethylene feed ratio higher than the first reactor so that a high ethylene conversion is obtained. The off gases of the second reactor are sent to a second water scrubber to remove and recover the additional ethylene oxide produced. The second scrubber off gases are split into two portions - one is recycled back to the first oxidation reactor while the other is purged, typically via incineration.

Figure 3:
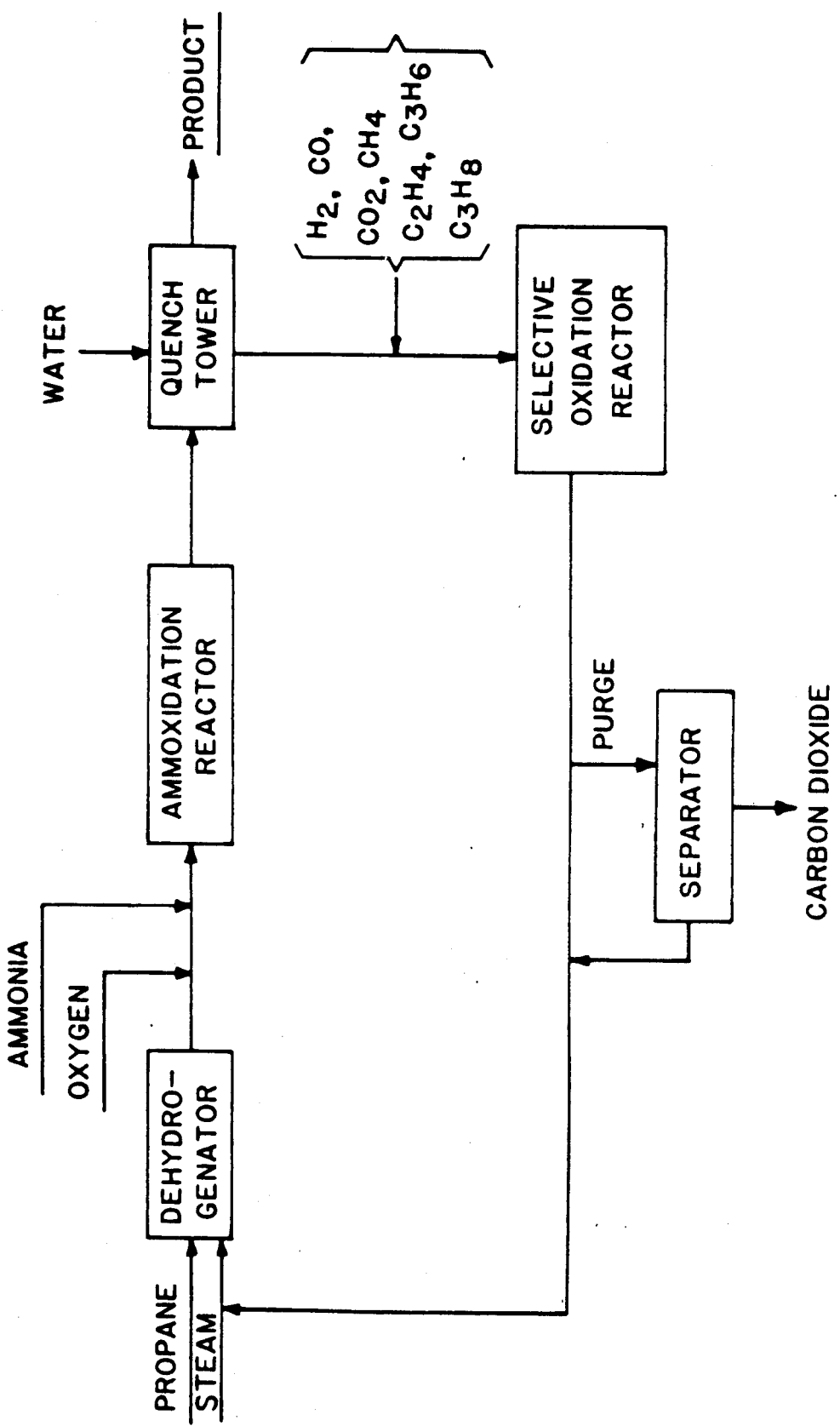
FIG. 3 illustrates in a block diagram a prior art process of producing acrylonitrile utilizing a recycle step.

FIG. 3 illustrates the cyclic process for producing acrylonitrile disclosed in Khoobiar et al U.S. Pat. No. 4,609,502. In this process, propane and steam are fed into a dehydrogenator to form propylene which is then mixed with oxygen and ammonia and fed into an ammoxidation reactor. The product is fed to an aqueous quench tower similar to that shown in FIG. 1 and the products withdrawn in solution. The gaseous take-off from the quench tower, typically containing oxygen, hydrogen, carbon monoxide, carbon dioxide, methane, ethane, ethylene, propane and propylene, is fed to a selective oxidation reactor. As previously indicated, it is generally essential for the efficient operation of such a reactor to heat the gas mixture prior to introduction therein.

A portion of the off-gas from the oxidation reactor is passed to a separator to remove carbon oxides by an undisclosed mechanism. A portion of the separator effluent, which contains light hydrocarbons and hydrogen, is purged, treated to remove propane and propylene and discarded thereby preventing buildup of by-products in the system.

The propane and propylene are combined with the remainder of the oxidator effluent and the remainder of the separator effluent and recycled to the dehydrogenator. It is, of course, necessary for the oxidator to be effective in removing all oxygen from the quench tower effluent to prevent significant loss of effectiveness of the dehydrogenator. It is also necessary for the oxygen feed to be pure oxygen since the use of air or oxygen-enriched air would produce a rapid accumulation of nitrogen in the system. This would, in turn, require the purging of a larger portion of the recycle stream with resulting loss of efficiency.

Figure 4:
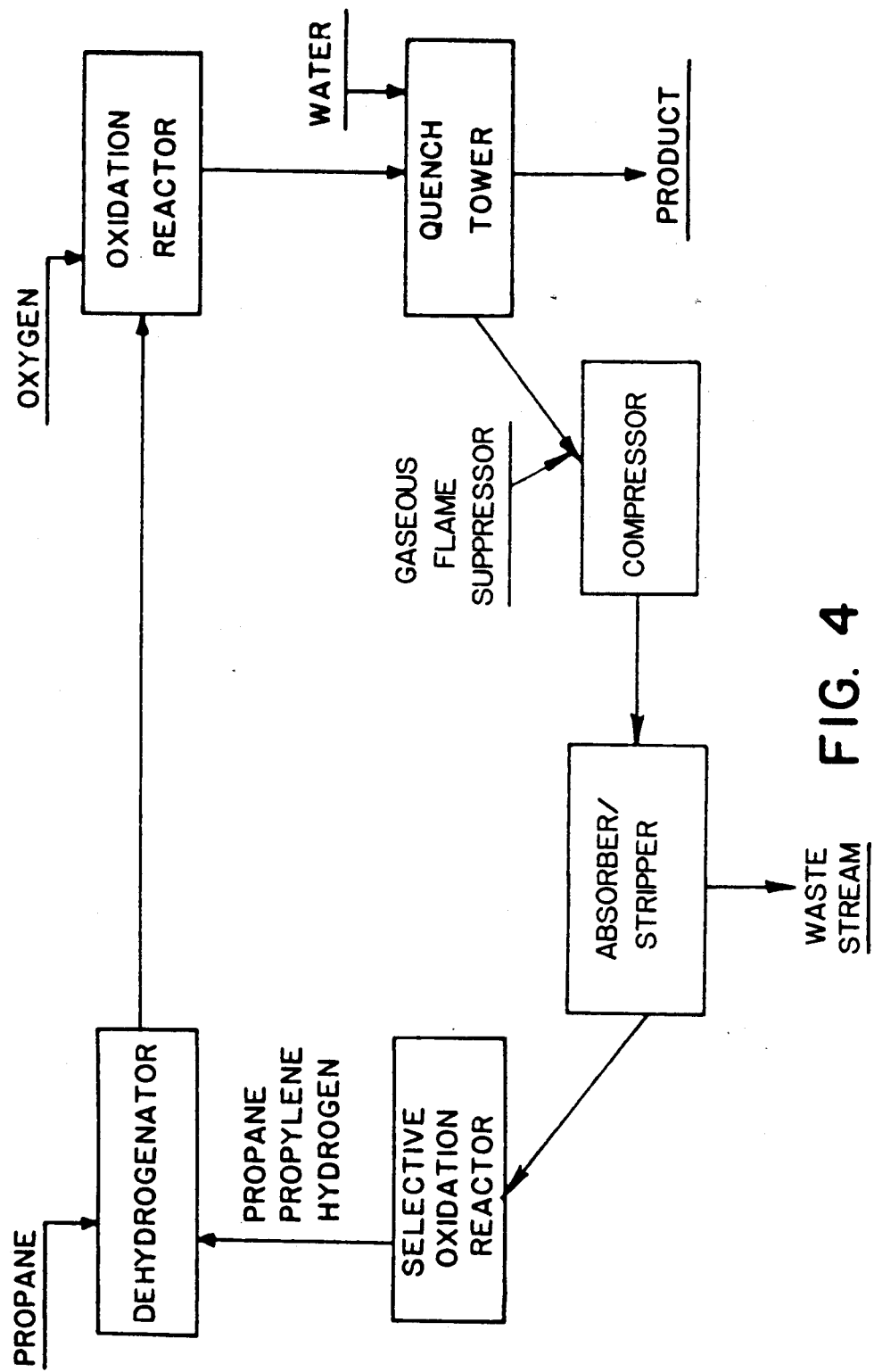
FIG. 4 illustrates in a block diagram the process of the invention for producing propylene oxide showing the addition of a flame suppressor.

The process of the present invention is illustrated in FIG. 4. The present process provides the efficiency of recycle afforded by the process illustrated in FIG. 3 and is similar in a generic sense in that it contains the same kinds of functional units, yet is substantially more efficient and, unexpectedly, capable of effectively utilizing air or oxygen-enriched air as a feed to the oxidation reactor. Specifically, the subject process utilizes an absorber/stripper unit under pressure to effectively remove carbon oxides, nitrogen if present, oxygen, hydrogen and light hydrocarbons from the quench tower gaseous effluent. It has been found that, in order to minimize the flammability potential of the waste stream from the absorber/stripper, the total hydrocarbon content of the gaseous mixture entering the compressor or the absorber/stripper must be maintained at a certain level relative to the pressure and oxygen content of the streams. This relationship, referred to herein as the "nonflammability index", is defined below. This is accomplished by adjusting the operating parameters of the cycle and, where necessary, adding an appropriate amount of a gaseous flame suppressor to the system. Although the gaseous flame suppressor can be added at any convenient point in the system, it is preferred that it be added to the quench tower gaseous effluent. The gaseous flame suppressor is methane or ethane, preferably the former.

As a result of the absorber/stripper unit being effective to remove all but about one percent of the oxygen in the quench tower gaseous effluent, the selective oxidation reactor can be comparatively small in terms of capital expenditure and have a long life, yet still effectively remove the oxygen from the recycle feed to the dehydrogenator. The configuration of the subject process eliminates the substantial loss of efficiency resulting from the use of the purge stream inherent in the process of FIG. 3.

In accordance with this invention, it has been found that operation of the system outside of the flammability range is possible by maintaining the nonflammability index of the stream entering the compressor utilized to raise the pressure for the absorber/stripper unit, and the waste stream for the absorber/stripper unit as well, within certain well-defined limits. The nonflammability index (NFI) is determined by the following expression $$NFI = \frac{\text{Percent Total Hydrocarbons}}{(\text{Pressure-psia})^{0.65} (\text{Percent Oxygen})^{1.94}}$$

wherein the exponents 0.65 and 1.94 are regression constants determined on the basis of experimental data relating to the flammability of oxygen/hydrocarbon mixtures and all percents are by volume.

The total hydrocarbon content is comprised of the reactant alkane and alkene, other lower hydrocarbons as may be present in the quench tower gaseous effluent and the gaseous flame suppressor, when present. The critical streams for determining total hydrocarbon content in accordance with the present invention are the feed lines to the compressor and the absorber/stripper unit as well as the waste stream produced therein. The high percentage of hydrocarbon reduces the ratio of oxygen to hydrocarbon in the mixture and, therefore, the flammability potential thereof.

Utilizing the above expression, it has been found that the NFI must be between about 0.005 and 10.0, preferably between about 0.0085 and 1.0. In the event that the operating parameters do not bring the NFI within the specified ranges and the adjustments required to do so are not advantageous to the overall economy of the process for other reasons, a sufficient quantity of gaseous flame suppressor is added to the quench tower gaseous effluent. It will be appreciated that the above determinations can be made by automated sensing apparatus and the results fed into suitable processor equipment which regulates the flow of gaseous flame suppressor into the quench tower gaseous effluent. It will also be appreciated that, although determinations can be carried out on any of the aforementioned streams, the critical stream in terms of total hydrocarbon content is the absorber/stripper waste stream since that is point of highest flammability potential in the system.

Referring to FIG. 4, propane is fed into the dehydrogenator where it is converted to propylene. For increased catalyst life, it is preferred to introduce a hydrogen-containing gas into the dehydrogenator with the propane feed, preferably, as a discrete stream. The catalyst utilized in the dehydrogenator can be any conventional dehydrogenation catalyst, preferably one or more Group VIII noble metals such as platinum on an alumina support. The dehydrogenator may be of any conventional design. The effluent product stream from the dehydrogenator comprising unreacted propane, propylene and hydrogen, is fed into a conventional oxidation reactor along with pure oxygen, air or, preferably, oxygen-enriched air and ammonia.

The oxidation reactor utilized in the present process is conventional and may employ either a fixed, fluidized or slurry reactor and appropriate catalyst. The reaction may be carried out either in gas or liquid phase. If it is carried out in a liquid phase, a suitable solvent may also be employed. The reactor may contain a suitable oxidation catalyst such as silver oxide, molybdenum oxide, ruthenium oxide, or lanthanum oxide, alone or in combination with others, and they may be supported or unsupported. Various catalysts are disclosed, for example, in Fenton, U.S. Pat. No. 3,316,279, Waddan et al., European Patent Appln. No. 0 043 192, Bryce Smith, Great Britain Patent 1,409,421, Bobolev, Great Britain Patent Nos. 1,433,885, and 1,433,886, Kolombos et al., U.S. Pat. No. 3,888,889, and Pennington, U.S. Pat. No. 4,785,123. Additional suitable catalysts are known to those skilled in the art.

The oxidation reaction is conducted at a temperature of from about 100° to 600° C., preferably from about 150° to 500° C.; at a pressure typically in the range of from about 10 to 1000 psig, preferably from about 150 to 750 psig. The reactor residence times vary depending upon the catalyst, as is well known to those skilled in the art, and it can be anywhere from a few seconds up to 1 hour. The oxygen-containing gas feed may be pure oxygen, air or oxygen-enriched air. In accordance with this invention, oxygen-enriched air preferably contains from about 30 to about 80, most preferably from about 55 to 65, percent by volume of oxygen. Such mixtures may be produced by adjusting the capacity of a conventional oxygen-producing unit, e.g. a conventional PSA system, or by mixing pure oxygen with air in the proper proportions. The ratio of oxygen to propylene in the feed converted to products is suitably in the range of from about 0.8:1 to 2.0:1 by volume.

The effluent from the oxidation reactor comprises a major amount of propylene oxide and minor amounts of acetone, acetaldehyde, formaldehyde, carbon oxides and nitrogen, when present in the feed, as well as unreacted oxygen, propylene and propane. The amounts and ratios of these products will, of course, depend on the catalyst used. This gaseous mixture is quenched or scrubbed with a liquid, such as water or an organic solvent, to dissolve the soluble compounds for subsequent separation and recovery of the desired compounds.

The gas phase effluent from the quench step is introduced under pressure into an absorber/stripper unit. A compressor or other suitable means is utilized to raise the pressure of the quench tower gaseous effluent to an effective level for the absorber/stripper, i.e. from about 20 to 100 psig, preferably from about 25 to 50 psig. The absorber/stripper unit is of a conventional type containing a liquid hydrocarbon such as, for example, heptane or octane. The quench tower effluent is introduced into the unit under pressure to force the gaseous hydrocarbons into solution. The gaseous hydrocarbons are recovered by lowering the pressure and, preferably, heating the liquid hydrocarbon. The flame suppressor, when present, is initially released and combined with the other gases which were not absorbed by the unit, i.e. oxygen, carbon oxides, (carbon monoxide and carbon dioxide), hydrogen and nitrogen when the feed to the oxidation reactor is air or oxygen-enriched air. These combined gases form a waste stream which is preferably incinerated, thereby recovering energy, e.g. to operate the compressor.

The second stream produced by the absorber/stripper unit is a recycle stream containing the unreacted alkane and alkene, i.e. propane and propylene, as well as a minor quantity of oxygen, typically less than about one percent by volume, and a minor quantity of nitrogen if present in the feed to the oxidation reactor. This recycle stream is introduced into the selective oxidation reactor.

The selective oxidation reactor is of conventional configuration and contains an art-recognized catalyst capable of selectively catalyzing the reaction of oxygen and hydrogen to form water, i.e. the oxidation of hydrogen, without causing oxidation of the desired hydrocarbons, i.e. propane and propylene in the absorber/stripper effluent. Such catalysts and their use are well known in the art. Suitable catalysts include noble metals or base metals, particularly platinum or palladium on alumina.

As previously stated, the oxidation reactor utilized in the present process requires only a very modest capital expenditure in comparison with the multiple bed unit contemplated in the process illustrated in FIG. 3 since the absorber/stripper effluent in the subject process contains less than one percent by volume of oxygen. Typically, the oxygen content of the absorber/stripper effluent in the present process is on the order of from about 0.01 to 1 percent by volume. Since the oxygen content is at such a low level, a small oxidation reactor consisting of a single bed without the need for catalyst regeneration over a period of several years is more than adequate in the method of this invention.

Utilizing a system as shown in FIG. 4 for the production of propylene oxide utilizing propane as the starting material, the flow rates at various points in the system were determined and are presented in Table I. The flow rates are expressed in mole percent based on 100 moles of propylene oxide produced. The propane feed was virtually 100 percent propane. The fresh feed added to the dehydrogenator effluent prior to introduction into the oxidation reactor was pure oxygen. Pure methane (commercial purity can be utilized as well) was added to the quench tower effluent as a flame suppressor. The data expressed in Table I represents operation of the system under conditions such that 20 percent of the propylene in the feed to the oxidation reactor is converted to different products, including propylene oxide.

In Table I, Point A is the feed into the dehydrogenator after the stream from the selective oxidation reactor has been combined with fresh propane, Point B is the combined feed into the oxidation reactor, Point C is the oxidation reactor effluent, Point D is the quench tower gaseous effluent to the absorber/stripper unit after the flame suppressor has been combined therewith, Point E is the recycled stream from the absorber/stripper unit and Point F is the absorber/stripper unit waste stream. As previously mentioned, the amount of hydrogen in the feed to the dehydrogenator will vary with the catalyst and reaction conditions used, and may be negligible. For purposes of the comparative results given in Tables I and II, hydrogen was not included in the dehydrogenator feed, Point A. In Tables I and II, methane was added prior to point D to maintain the NFI at approximately 0.0085 at point F.

TABLE I

PROPYLENE OXIDE FROM PROPANE
100% $O_2$ FEED
PROPANE CONVERSION = 40%
PROPYLENE CONVERSION = 20%
NO $H_2$ RECOVERY

| COMPONENT | A | B | C | D | E | F |
|---|---|---|---|---|---|---|
| $C_3H_6$ | 51.8 | 50.2 | 39.1 | 43.0 | 63.6 | 6.0 |
| $C_3H_8$ | 45.4 | 20.1 | 19.5 | 21.5 | 32.5 | 1.8 |
| $O_2$ | 0.0 | 14.3 | 2.0 | 4.4 | 0.3 | 11.8 |
| PO | — | — | 6.8 | — | — | — |
| ACETONE | — | — | 0.6 | — | — | — |
| $C_2H_5COOH$ | — | — | 0.3 | — | — | — |
| HCHO | — | — | 0.6 | — | — | — |
| $CH_3CHO$ | — | — | 0.3 | — | — | — |
| CO | 0.2 | 0.1 | 3.1 | 3.4 | 0.2 | 9.0 |
| $CO_2$ | 1.3 | 1.0 | 5.3 | 5.9 | 1.6 | 13.5 |
| $H_2O$ | — | — | 8.4 | — | — | — |
| $CH_4$ | 0.8 | 1.1 | 1.1 | 7.7 | 1.0 | 19.9 |
| $C_2H_4$ | 0.1 | 0.2 | 0.2 | 0.2 | 0.1 | 0.4 |
| $C_2H_6$ | 0.4 | 1.0 | 0.9 | 1.0 | 0.5 | 2.0 |
| $H_2$ | 0.0 | 12.0 | 11.7 | 12.9 | 0.3 | 35.6 |

TABLE I-continued

| | | | | | | |
|---|---|---|---|---|---|---|
| $N_2$ | 0.0 | 0.0 | 0.0 | 0.0 | 0.0 | 0.0 |
| TOTAL MOLES | 1048.4 | 1423.4 | 1465.9 | 1329.4 | 853.9 | 475.5 |

Again utilizing a system as shown in FIG. 4 for the production of propylene oxide with propane as a starting material, the oxygen feed to the oxidation reactor was changed to an equal mixture of pure oxygen and air which produced oxygen-enriched air containing approximately 60 percent by volume of oxygen. The flow rates at various points in the system were determined and are presented in Table II. The data expressed in Table II represents operation of the system under conditions such that 20 percent of the propylene in the feed to the oxidation reactor is converted therein to different products, including propylene oxide.

TABLE II

PROPYLENE OXIDE FROM PROPANE
50% $O_2$ + 50% AIR FEED
PROPANE CONVERSION = 40%
PROPYLENE CONVERSION = 20%
NO $H_2$ RECOVERY

| COMPONENT | A | B | C | D | E | F |
|---|---|---|---|---|---|---|
| $C_3H_6$ | 51.7 | 45.7 | 35.7 | 39.5 | 63.4 | 4.8 |
| $C_3H_8$ | 45.4 | 18.3 | 17.9 | 19.8 | 32.4 | 1.5 |
| $O_2$ | 0.0 | 13.2 | 2.0 | 4.4 | 0.3 | 10.4 |
| PO | — | — | 6.2 | — | — | — |
| ACETONE | — | — | 0.5 | — | — | — |
| $C_2H_5COOH$ | — | — | 0.3 | — | — | — |
| HCHO | — | — | 0.5 | — | — | — |
| $CH_3CHO$ | — | — | 0.3 | — | — | — |
| CO | 0.2 | 0.1 | 2.8 | 3.1 | 0.2 | 7.3 |
| $CO_2$ | 1.3 | 0.9 | 4.9 | 5.4 | 1.6 | 10.9 |
| $H_2O$ | — | — | 7.7 | — | — | — |
| $CH_4$ | 0.6 | 0.9 | 0.9 | 5.3 | 0.7 | 11.8 |
| $C_2H_4$ | 0.1 | 0.2 | 0.2 | 0.2 | 0.1 | 0.3 |
| $C_2H_6$ | 0.4 | 0.9 | 0.9 | 1.0 | 0.5 | 1.6 |
| $H_2$ | 0.0 | 10.9 | 10.7 | 11.8 | 0.3 | 28.6 |
| $N_2$ | 0.4 | 8.9 | 8.6 | 9.6 | 0.4 | 22.8 |
| TOTAL MOLES | 1049.4 | 1561.8 | 1608.5 | 1445.9 | 855.7 | 590.2 |

Figure 5:
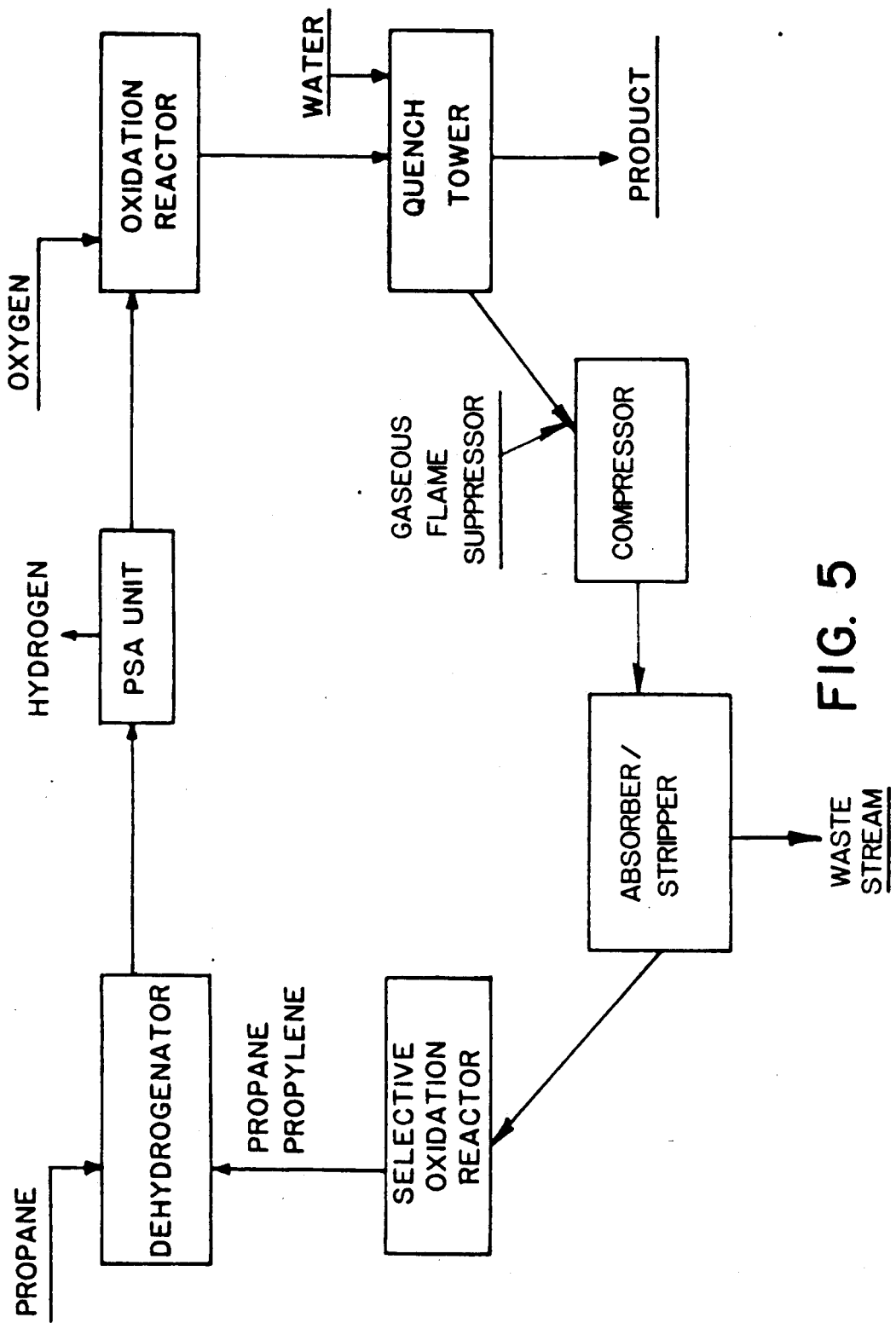
FIG. 5 illustrates in a block diagram the process as shown in FIG. 4 additionally incorporating a means of recovering hydrogen from the dehydrogenator effluent.

In an embodiment of the present invention shown in FIG. 5, the hydrogen from the dehydrogenator effluent is removed prior to introduction into the oxidation reactor. Since hydrogen will be removed in the absorber/stripper unit, removing it from the dehydrogenator effluent provides an additional product and recycle hydrogen where it is required in the system, i.e. the selective oxidating unit and the dehydrogenator itself. The removing of hydrogen from the dehydrogenator effluent may be carried out conventionally in an absorber or, preferably, in a PSA unit.

PSA is a well known process for separating the components of a mixture of gases by virtue of the difference in the degree of adsorption among them on a particular adsorbent retained in a stationary bed. Typically, two or more such beds are operated in a cyclic process comprising adsorption under relatively high pressure and desorption or bed regeneration under low pressure or vacuum. The desired component or components may be obtained during either of these stages. The cycle may contain other steps in addition to the fundamental steps of adsorption and regeneration, and it is commonplace to have two or more adsorbent beds cycled out of phase to assure a pseudo continuous flow of desired product.

The PSA unit contains an adsorbent, such as silica gel or activated carbon, which will strongly adsorb $C_3$ hydrocarbons, i.e., propane and propylene, and allow hydrogen to pass through. This hydrogen may be further purified to produce a high-purity hydrogen stream which may be taken as product or vented. It is within the scope of the present invention to at least partially recycle the hydrogen stream to the dehydrogenator as discussed, or to the selective oxidation reactor.

Using a system as shown in FIG. 5 for the production of propylene oxide using propane as the starting material, the flow rates at various points in the system are shown in Table III. The propane and pure oxygen feeds were as in Table I. In Table III, the operation of the system is illustrated for a 20 percent conversion of propylene to products, including propylene oxide.

In Table III, Point A is the feed to the dehydrogenator after the recycle stream from the selective oxidation reactor has been combined with fresh propane, Point B is the dehydrogenator effluent prior to introduction into the PSA unit, Point C is the combined feed into the oxidation reactor, Point D is the oxidation reactor effluent, Point E is the quench tower gaseous effluent to the absorber/stripper unit after the flame suppressor has been combined therewith and Point F is the absorber/stripper waste stream.

TABLE III

PROPYLENE OXIDE FROM PROPANE
100% $O_2$ FEED
PROPANE CONVERSION = 40%
PROPYLENE CONVERSION = 20%
WITH $H_2$ RECOVERY

| COMPONENT | A | B | C | D | E | F |
|---|---|---|---|---|---|---|
| $C_3H_6$ | 52.1 | 58.8 | 56.2 | 43.6 | 50.1 | 9.7 |
| $C_3H_8$ | 46.0 | 23.5 | 22.2 | 21.6 | 24.8 | 2.9 |
| $O_2$ | 0.0 | — | 15.8 | 2.0 | 4.6 | 17.0 |

TABLE III-continued

| | | | | | | |
|---|---|---|---|---|---|---|
| PO | — | — | — | 7.6 | — | — |
| ACETONE | — | — | — | 0.7 | — | — |
| $C_2H_5COOH$ | — | — | — | 0.3 | — | — |
| HCHO | — | — | — | 0.7 | — | — |
| $CH_3CHO$ | — | — | — | 0.3 | — | — |
| CO | 0.2 | 0.1 | 0.1 | 3.4 | 3.9 | 14.3 |
| $CO_2$ | 1.3 | 1.1 | 1.1 | 6.0 | 6.8 | 21.7 |
| $H_2O$ | — | — | — | 9.3 | — | — |
| $CH_4$ | 0.5 | 1.1 | 0.8 | 0.7 | 5.5 | 19.5 |
| $C_2H_4$ | 0.1 | 0.2 | 0.1 | 0.1 | 0.2 | 0.4 |
| $C_2H_6$ | 0.4 | 1.1 | 1.1 | 1.0 | 1.2 | 3.1 |
| $H_2$ | 0.0 | 14.0 | 2.7 | 2.6 | 3.0 | 11.4 |
| $N_2$ | 0.0 | 0.0 | 0.0 | 0.0 | 0.0 | 0.0 |
| TOTAL MOLES | 1043.4 | 1214.8 | 1271.6 | 1309.6 | 1141.0 | 295.6 |

Again, utilizing a system as shown in FIG. 5 for the production of propylene oxide with propane as the starting material the oxygen feed to the oxidation reactor was changed to an equal mixture of pure oxygen and air which produced oxygen-enriched air containing approximately 60 percent by volume of oxygen. The flow rates at various points in the system were determined and are presented in Table IV. The data expressed in Table IV represents operation of the system under conditions such that 20 percent, of the propylene in the feed to the oxidation reactor is converted therein to different products, including propylene oxide.

TABLE IV

PROPYLENE OXIDE FROM PROPANE
50% $O_2$ + 50% AIR FEED
PROPANE CONVERSION = 40%
PROPYLENE CONVERSION = 20%
WITH $H_2$ RECOVERY

| COMPONENT | A | B | C | D | E | F |
|---|---|---|---|---|---|---|
| $C_3H_6$ | 52.1 | 58.8 | 50.8 | 39.6 | 45.8 | 7.1 |
| $C_3H_8$ | 45.7 | 23.5 | 20.1 | 19.6 | 22.7 | 2.1 |
| $O_2$ | 0.0 | — | 14.4 | 2.0 | 4.6 | 13.8 |
| PO | — | — | — | 6.9 | — | — |
| ACETONE | — | — | — | 0.6 | — | — |
| $C_2H_5COOH$ | — | — | — | 0.3 | — | — |
| HCHO | — | — | — | 0.6 | — | — |
| $CH_3CHO$ | — | — | — | 0.3 | — | — |
| CO | 0.2 | 0.1 | 0.1 | 3.1 | 3.5 | 10.6 |
| $CO_2$ | 1.3 | 1.1 | 1.0 | 5.4 | 6.3 | 16.0 |
| $H_2O$ | — | — | — | 8.5 | — | — |
| $CH_4$ | 0.2 | 0.8 | 0.5 | 0.5 | 2.4 | 6.9 |
| $C_2H_4$ | 0.1 | 0.2 | 0.1 | 0.1 | 0.1 | 0.3 |
| $C_2H_6$ | 0.4 | 1.1 | 1.0 | 0.9 | 1.1 | 2.3 |
| $H_2$ | 0.0 | 14.0 | 2.4 | 2.3 | 2.7 | 8.3 |
| $N_2$ | 0.3 | 0.3 | 9.6 | 9.3 | 10.8 | 32.6 |
| TOTAL MOLES | 1043.8 | 1215.3 | 1406.7 | 1444.86 | 1248.0 | 401.5 |

Figure 6:
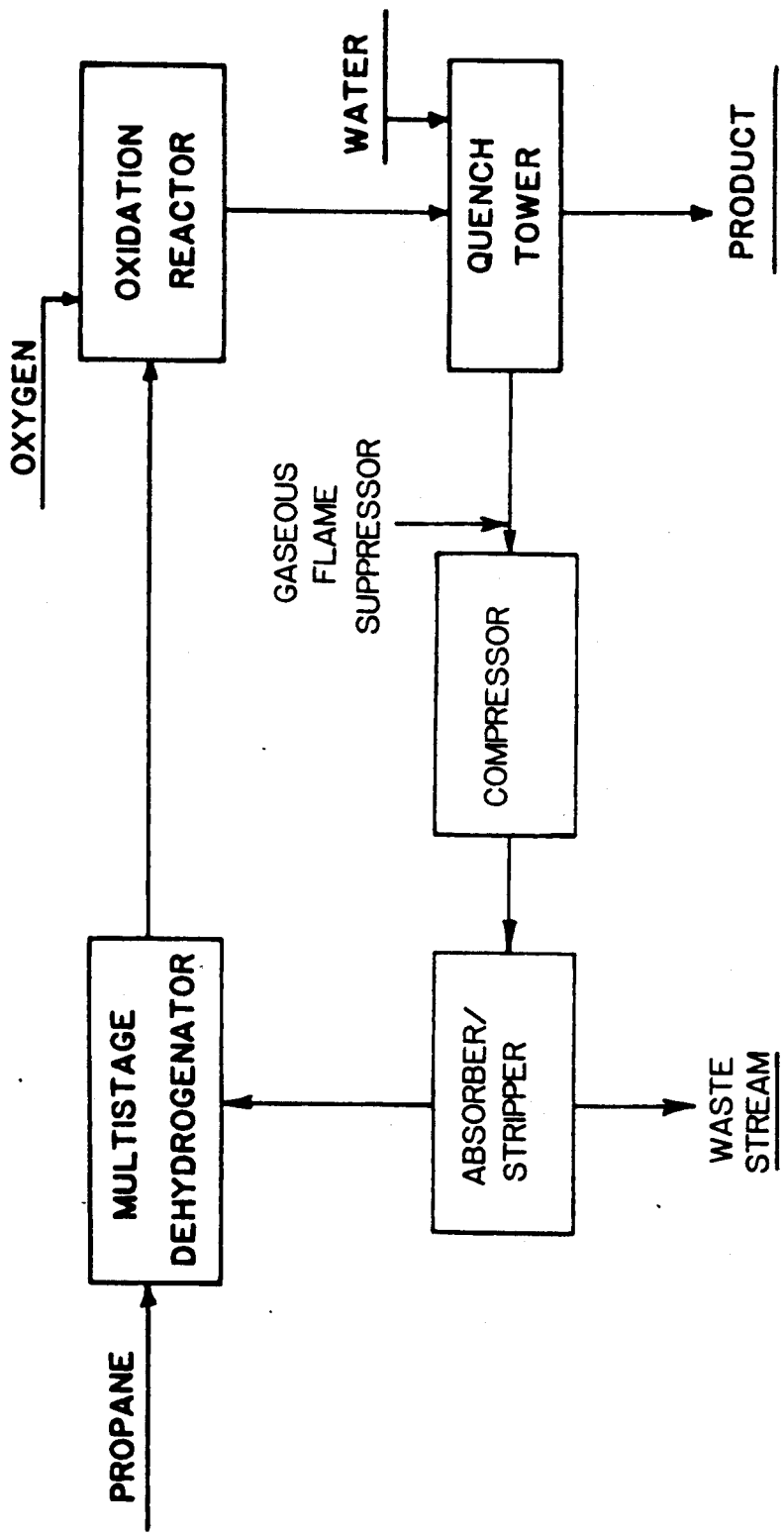
FIG. 6 illustrates in a block diagram the process of the invention with the addition of a flame suppressor incorporating a multistage dehydrogenator without a selective oxidation unit.

Turning to FIG. 6, the dehydrogenator utilized is a multistage unit which eliminates the need for the selective oxidation reactor. The use of a multistage catalytic reactor is described in the literature, e.g. Pujado et al in a paper entitled "Catalytic Conversion of LPG" presented at the American Institute of Chemical Engineers, Apr. 6-10, 1986. In such reactors, the catalyst sequentially flows through a series of discrete reactors and is withdrawn at the end for regeneration and recycle. The reactant gas stream likewise flows through the reactors and is withdrawn into a heating means between each of the individual reactors. The dehydrogenator typically operates at a temperature of from about 500° to 800° C., preferably from about 600° to 700° C. The reheating of the reactant stream as it flows through the reactors is especially beneficial for an endothermic reaction such as the conversion of propane to propylene.

In the multistage dehydrogenator shown in FIG. 6, the reactant gas stream does not flow through all of the reactors, but is withdrawn as a product stream intermediate the first and last reactors. Preferably, there are at least four reactors and the product stream is withdrawn from the penultimate reactor. It is beneficial to withdraw the product stream from a latter stage of the dehydrogenator to obtain maximum efficiency therefrom. The reheating of the reactor stream takes place only up to and including the reactor from which the product stream is withdrawn.

The recycle product stream from the absorber/stripper unit of the present invention, which is comprised of unreacted alkane and alkene and a minor amount of oxygen, is introduced into the reactor following that from which the product stream is withdrawn, passed therethrough and through subsequent reactors, if any. The low oxygen content thereof can be eliminated without detriment to the system. Therefore, the selective oxidator present in the embodiments of the present invention shown in FIGS. 4 and 5 can be eliminated. The detail of the multistage dehydrogenator utilized in accordance with the present invention is shown in FIG. 7.

Figure 7:
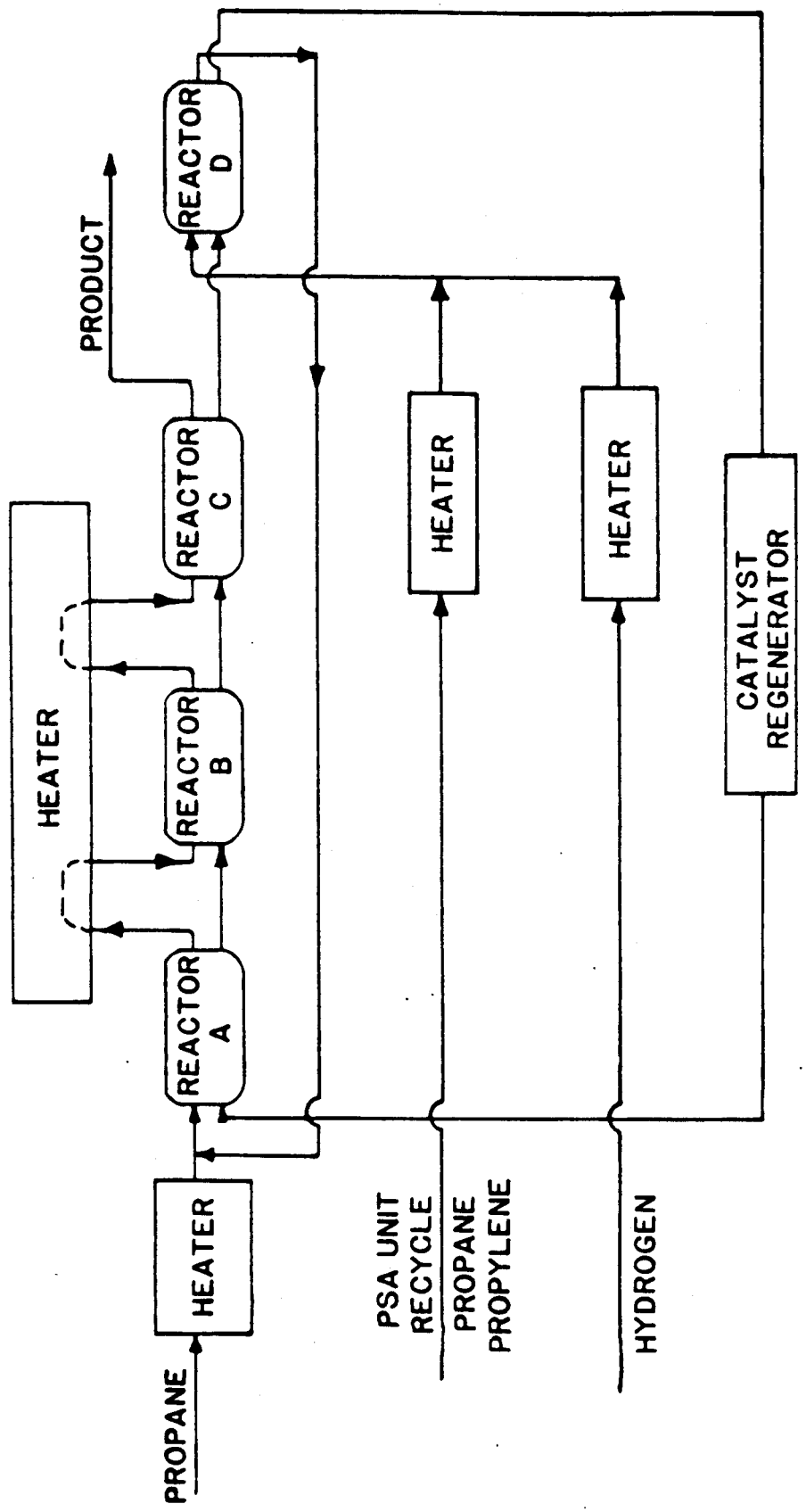
FIG. 7 illustrates in a block diagram detail of the multistage dehydrogenator of FIG. 6.

In the embodiment shown in FIG. 7, the effluent from the final reactor of the dehydrogenator is introduced into the initial feed stream. In the event that the feed to one of the intermediate reactors more closely approximates the effluent in regard to the concentration of the alkene than the initial feed, the effluent is introduced into such intermediate reactor. It is further contemplated to introduce the effluent from the final reactor directly into the oxidation reactor if the alkene content thereof is sufficiently high. This might occur, for example, when the absorber/stripper effluent passed through two or more reactors of the dehydrogenator.

It is contemplated herein to add a PSA unit on the effluent from the dehydrogenator to remove hydrogen therefrom. The hydrogen thus obtained may be vented, recycled to the dehydrogenator feed or supplied to the heater in combination with an oxygen feed for combustion. It will be appreciated by those skilled in the art that a single heater can be utilized in FIG. 7 with all streams flowing therethrough.

The process of this invention is advantageous in that it is very efficient and is cost attractive in comparison to prior art processes. It is readily apparent from the data presented herein that, in contrast to the subject process, the process illustrated in FIG. 3 continually removes propane and propylene from the system, thereby sharply reducing the efficiency thereof. It is stated in the Khoobiar et al patent that propane and propylene are removed from the purge stream before it is vented. This would require an additional sizable capital expenditure for the refrigeration equipment required for the recovery procedure as well as an on-going cost in power to operate the recovery unit. The process of the invention has a comparatively small incidence of build-up of any of the components of the various gaseous streams formed or separated at any stage thereof. The subject process can be utilized with air or an oxygen-enriched air feed, heretofore not feasible with a closed loop system. Unexpectedly, the subject process operates at particularly enhanced efficiency with an oxygen-enriched air feed.

Further, by maintaining the nonflammability index of certain streams within the limits set forth herein, by the addition of a gaseous flame suppressor if required, the subject process utilizes an absorber/stripper unit operating under pressure while eliminating the flammability potential thereof. The flame suppressor, when present, is merely added and withdrawn and can be combusted upon withdrawal to provide energy for the system, thereby realizing an additional economic benefit.

The invention has been described with reference to preferred embodiments thereof. It will be appreciated by those skilled in the art that various modifications may be made from the specific details given without departing from the spirit and scope of the invention.

We claim:

1. A process for the production of alkylene oxides comprising:
   (a) forming an alkene from a gaseous alkane in a catalytic dehydrogenator;
   (b) introducing a gaseous stream comprising said alkene and pure oxygen, air or a gas-enriched in oxygen relative to air into a reactor and reacting them in the presence of an oxidation catalyst at a temperature in the range of about 100° to about 600° C. and a pressure of about 10 to about 100 psig, and a residence time of from a few seconds to about one hour to produce a gaseous effluent containing said alkylene oxide;
   (c) quenching said effluent in a liquid to form a liquid phase containing said alkylene oxide and a gaseous phase;
   (d) recovering said alkylene oxide from said liquid phase;
   (e) raising the pressure of the gaseous phase and introducing it into an absorber/stripper unit to thereby form a recycle gaseous stream comprising unreacted alkane and alkene, a minor amount of oxygen, and nitrogen, when air or oxygen-enriched air is introduced into the reactor in step (b), and a waste stream comprising the remainder of said gaseous effluent, wherein the nonflammability index of the waste stream formed in step (e), determined according to the expression:

$$\frac{\text{Nonflammability}}{\text{Index}} = \frac{\text{Percent Total Hydrocarbons}}{(\text{Pressure-psia})^{0.65} (\text{Percent Oxygen})^{1.94}}$$

is between about 0.005 and 10.0;
   (f) introducing the recycle stream into a catalytic selective oxidation unit to remove the remaining oxygen in said stream; and
   (g) introducing the recycle effluent from the selective oxidation unit into the dehydrogenator.

2. A process in accordance with claim 1, wherein a gaseous flame suppressor is added to the gaseous phase formed in step (c) to raise the total hydrocarbon content thereof so that the nonflammability index is within said range.

3. A process in accordance with claim 2, wherein the flame suppressor is selected from methane and ethane.

4. A process in accordance with claim 3, wherein the flame suppressor is methane.

5. A process in accordance with claim 1, wherein the alkane is propane, the alkene is propylene, the catalyst is an oxidation catalyst and the oxide produced is propylene oxide.

6. A process in accordance with claim 1, wherein oxygen is added in step (b) as pure oxygen.

7. A process in accordance with claim 1, wherein oxygen is added in step (b) as oxygen-enriched air containing from about 30 to about 80 percent of oxygen by volume.

8. A process in accordance with claim 1, wherein the pressure of the stream formed in step (c) is raised to from about 20 to 100 psig prior to introducing it into the absorber/stripper unit.

9. A process in accordance with claim 1, wherein the waste stream formed in step (e) contains said flame suppressor and is combusted.

10. A process in accordance with claim 1, wherein the nonflammability index of the quench tower gaseous effluent is between about 0.0085 and 1.0.

11. A process in accordance with claim 1, wherein the effluent from the catalytic dehydrogenator is passed through a PSA unit to remove hydrogen therefrom prior to being introduced into the reactor in step (b).

12. A process in accordance with claim 11, wherein the hydrogen removed in the PSA unit is at least partially recycled to the dehydrogenator.

13. A process in accordance with claim 1, wherein the catalytic dehydrogenator is composed of a series of at least three discrete catalytic reactors, the product stream containing said alkene and unreacted alkane is withdrawn from a reactor intermediate the first and last of said reactors, the gaseous flow between said reactors, including the reactor from which the product stream is withdrawn is passed through a heating means to raise the temperature thereof, the catalyst in the dehydrogenator is passed through all of said reactors regenerated and recycled to the first reactor, the recycle stream containing alkene, and unreacted alkane is passed directly from the absorber/stripper unit to the reactors in the dehydrogenator which follow in sequence the reactor from which the product stream was withdrawn thereby removing substantially all of the oxygen in said stream, and the effluent from said last reactor is introduced into the first reactor, a reactor other than the first reactor wherein the concentration of the alkene is approximately the same as that of said effluent or said reactor in step (b).

14. A process in accordance with claim 13, wherein the dehydrogenator contains at least four reactors and the product stream is withdrawn from the penultimate reactor.

15. A process in accordance with claim 13, wherein the effluent from said last reactor is introduced into the feed to said first reactor.

16. A process in accordance with claim 13, wherein the effluent from said last reactor is introduced into a reactor other than said first reactor wherein the concentration of the alkene is approximately the same as that of said effluent.

17. The process in accordance with claim 13, wherein the effluent from said last reactor is introduced into said reactor in step (b).

18. A process in accordance with claim 13, wherein the product stream withdrawn from the dehydrogenator is passed through a PSA unit to remove hydrogen therefrom prior to introduction into said reactor in step (b).

19. A process in accordance with claim 1, wherein the alkane is ethane, the alkene is ethylene, the catalyst is an oxidation catalyst and the oxide produced is ethylene oxide.

* * * * *

UNITED STATES PATENT AND TRADEMARK OFFICE
CERTIFICATE OF CORRECTION

PATENT NO. : 5,043,461
DATED : Aug. 27, 1991
INVENTOR(S) : Ramachandran et al

It is certified that error appears in the above-indentified patent and that said Letters Patent is hereby corrected as shown below:

Col. 13, line 57, delete "100" and substitute therefor --1000--.

Signed and Sealed this

Twenty-eighth Day of September, 1993

Attest:

BRUCE LEHMAN

Attesting Officer     Commissioner of Patents and Trademarks